(12) United States Patent
Liau

(10) Patent No.: US 7,232,578 B2
(45) Date of Patent: Jun. 19, 2007

(54) PHARMACEUTICAL COMPOSITION INDUCING CANCER CELL DIFFERENTIATION AND THE USE FOR TREATMENT AND PREVENTION OF CANCER THEREOF

(75) Inventor: Ming-Cheng Liau, Sugarland, TX (US)

(73) Assignee: Bio Grand Co., Ltd., Taipei (TW)

( * ) Notice: Subject to any disclaimer, the term of this patent is extended or adjusted under 35 U.S.C. 154(b) by 25 days.

(21) Appl. No.: 11/106,620

(22) Filed: Apr. 15, 2005

(65) Prior Publication Data

US 2005/0181065 A1 Aug. 18, 2005

(51) Int. Cl.
*A61K 35/12* (2006.01)
*A61K 35/22* (2006.01)
*A61K 31/525* (2006.01)
*A01N 43/60* (2006.01)

(52) U.S. Cl. .................. 424/545; 424/520; 514/251
(58) Field of Classification Search ............ 424/520, 424/545; 514/251
See application file for complete search history.

*Primary Examiner*—Johann Richter
*Assistant Examiner*—Konata M. George
(74) *Attorney, Agent, or Firm*—Rosenberg, Klein & Lee

(57) ABSTRACT

The present invention relates to a pharmaceutical composition for the treatment and prevention of cancer and the preparation method thereof, especially to a cell differentiation agent named CDA-II which is prepared by reverse phase chromatography of fresh human urine. The pharmaceutical composition is effective for the treatment and prevention of cancer. The active components in CDA-II contain differentiation inducers, differentiation helper inducers and an anticachexia agent, which act cooperatively to achieve the best therapeutic effect.

7 Claims, 7 Drawing Sheets

PHARMACEUTICAL COMPOSITION INDUCING CANCER CELL DIFFERENTIATION AND THE USE FOR TREATMENT AND PREVENTION OF CANCER THEREOF

BACKGROUND OF THE INVENTION

1. Field of the Invention

The present invention relates to a pharmaceutical composition used for treating and preventing cancers and the preparation thereof. More specifically, the present invention relates to a cell differentiation agent (CDA-II) obtained from fresh urine, and the method for the preparation thereof. The pharmaceutical composition according to the present invention is effective in treating and preventing cancers.

According to the present invention, CDA-II can correct the ternary methylation enzymes in cancer cells from their abnormal state, thereby promote terminal differentiation of the cancer cells to achieve desired therapeutic effects. This method for treating cancer aimed at eliminating the cause of the disease is effective as demonstrated by clinical trails. CDA-II antagonizes the function of a cancer specific protein bonded to the ternary methylation enzymes of cancer cells, therefore, the method of the present invention is highly selective and has no adverse effect. The active components of CDA-II comprise differentiation inducers, differentiation helper inducers and an anti-cachexia agent. These active components act synergistically to achieve therapeutic effect.

CDA-II has a better anticancer effect when combined with other anticancer drugs, such as thymidine.

Further, CDA-II has a very good anticancer effect when combined with vitamin C and vitamin $B_{17}$.

Cancer includes a variety of very complicated diseases; nevertheless, they all share a common feature that all cancer cells are able to keep on dividing, and can not undergo terminal differentiation. The present inventor has found that the abnormality of ternary methylation enzymes were the major cause of cancer disease, which provides a new strategy for cancer therapy. Cell differentiation agent, which is purified from the urine of normal persons, can transform abnormal ternary methylation enzymes in cancer cells to their normal forms. Thus cancer cells can be induced to undergo terminal differentiation, resulting in the termination of cell replication and/or apoptosis. In this way cancer can be cured. This treatment is safe to patients as the cell differentiation agent acts selectively on cancer cells. Furthermore, healthy persons also rely on this mechanism to fight against cancers. Accordingly, such a treatment of cancer is thus called "natural anticancer method".

The active components in cell differentiation agent include differentiation inducers and differentiation helper inducers. The differentiation inducer can eliminate the abnormal protein factor (i.e. abnormal tumor specific protein factor) bonded to the ternary methylation enzyme, which is present specifically in cancer cells. The differentiation helper inducer is the inhibitor of the component enzymes of the ternary methylation enzymes, which can potentiate the action of the differentiation inducer. In the cell differentiation agent according to the present invention, the differentiation inducers are PP-0 and OA-0.79, and differentiation helper inducers include 4-hydroxyphenylacetic acid, hippuric acid, 5-hyrdroxyindole acetic acid, uroerythrin and riboflavin. PP-0 is a peptide conjugated with a pigment material which emerges from a gel filtration column of Ultrogel AcA202 with a $K_{av}$, value of 0. OA-79 is an organic acid which emerges from the same gel column with a $K_{av}$ value of 0.79. In addition, the cell differentiation agent comprises an anti-cachexia component such as phenylacetylglutamine. Because most cancer patients develop the symptom of cachexia, anticachexia agent is helpful to the treatment of cancer. Briefly, the combination of the active components in the cell differentiation agent can provide excellent therapeutic effect. The present inventor further found that the cell differentiation agent of the present invention could give a better anticancer effect when used with the other cytotoxic drugs, such as thymidine. The present inventor also found that the cell differentiation agent of the present invention could also give a much better therapeutic effect when used together with vitamin C and vitamin $B_{17}$.

2. Description of the Prior Art

Oncogenes are parts of human genome; thus, there were human being, there were cancers. However, up to now cancer is still a problem to be overcome by human. Because of the complexity of cancer, it is very difficulty to eradicate cancer cells from the patient. Cancer cells keep on dividing, invade into normal organs and tissues, and finally cause serious diseases to result in death of the patient. Traditionally, the ability to keep on dividing is regarded as the major cause of cancer, and the therapy based thereon is the administration of cytotoxic drugs, which can inhibit the synthesis of DNA and the division of cells. For the last five decades, therapy of cancer has been developed mainly on the technology of using cytotoxic drugs. New therapy of cancer is thus desirable.

Retinoic acid is a differentiation inducer successfully used in the treatment of acute promyelocytic leukemia (Huang et al., 1988; Warrell et al., 1991, ref. 8 and 28). Although it has an excellent anti-cancer effect, cancer cells recur soon (Muindi et al., 1992; Adamson, et al., 1993, ref. 1 and 25). The recurrence is caused by the incompleteness of differentiation associated with the use of differentiation inducer alone. The use of differentiation inducer alone results in the damage of the cell, making it impossible to complete the differentiation processes.

REFERENCES CITED

The references cited in and/or relevant to the present invention are listed below:
1. Adamson P. C., Boylan J. F., Balis F. M., Murfy R. F., Godwin K. A., Gudas L. T., Poplack D. G., Time course of induction of metabolism of all-trans retinoic acid and the up-regulation of cellular retinoic acid binding protein, Cancer Res., 53: 472-476, 1993.
2. Bar-Or D., Greisman S. L., Kastendieck J. G., Detection of appendicitis by measurement of uroerythrin, U.S. Pat. No. 5,053,389, 1991.
3. Borek E., et al., Altered excretion of modified nucleosides and [bgr]-aminoisobutyric acid in subjects with acquired immunodeficiency syndrome or at risk for acquired immunodefociency syndrome, Cancer Res., 46: 2557, 1986.
4. Burzynski, S. R., Treatment of Malignant Brain tumors with Antineoplastons, Adv. Exp. Clin. Chemother, 6/88: 45-46, 1988.
5. Clark P. M. S., Kricka L. J., Whitehead T. P., Pattern of urinary proteins and peptides with rheumatioid arthritis investigated with the iso-Dalt technique, Clin. Chem., 26:201, 1980.
6. Doerfler, W., DNA methylation and gene activity, Annu. Rev. Biochem., 52: 92-124, 1983.
7. Epifanova, O. I., Abuladze, M. K., and Zoniovska, A. I., Effect of low concentrations of actinomycin D on the initiation of DNA synthesis in rapidly proliferating and stimulated cell culture, Exp. Cell Res., 92: 25-30, 1975.

8. Huang, M. E., Ye, Y. C., Chen, S. R., Chai, J. R., Lu, J. X., Zhao, L., Gu, L. J. and Wang, Z. Y, Use of all-trans retinoic acid in the treatment of acute promyelocytic leukemia, Blood, 72: 567-572, 1988.
9. Jones, P. A., Altering gene expression with 5-azacytidine, Cell, 40, 484-486, 1985.
10. Kampalath, B. N., Liau, M. C., Burzynski, B., and Burzynski, S. R., Chemoprevention by Antineoplaston A10 of Benzo (a) pyrene-induced Pulmonary Neoplasia, Drugs Exptl. Clin. Res., 13(supplement): 51-56, 1987.
11. Liau, M. C., who is the same inventor of this application case, Smith, D. W., and Hurlbert, R. B., Preferential inhibition by homopoly ribonucleotides of the methylation of ribosomal ribonucleic acid and disruption of the production of ribosomes in a rat tumor, Cancer Res., 35: 2340-2349, 1975.
12. Liau, M. C., Hunt, M. E. and Hurlbert, R. B., Role of ribosomal RNA methylases in the regulation of ribosome production in mammalian cells, Biochem., 15: 3158-3164, 1976.
13. Liau, M. C., Lin, G. W., and Hurlbert, R. B., Partial purification and characterization of tumor and liver S-adenosylmethionine synthetase, Cancer Res., 37: 427-435, 1977.
14. Liau, M. C., Lin G. W., Knight, C. A., and Hurlbert, R. B., Inhibition of RNA Methylation by Intercalating Agents, Cancer Res., 37: 4202-4210, 1977.
15. Liau, M. C., Chang, C. F., and Becker, F. F., Alteration of S-adenosylmethionine synthetase during chemical hepatocarcinogenesis and in resulting carcinomas, Cancer Res., 39: 2113-2119, 1979.
16. Liau, M. C., and Burzynski, S. R., Altered methylation complex isozymes as selective targets for cancer chemotherapy, Drugs Exptl. Clin. Res., 12(supplement): 77-86, 1986.
17. Liau, M. C., Szopa, M., Burzynski, B., and Burzynski, S. R., Chemosurveillance; a novel concept of the natural defense mechanism against cancer, Drugs Exptl. Clin. Res., 12(supplement): 71-76, 1987.
18. Liau, M. C., Lee S. S., and Burzynski, S. R., Differentiation inducing components of antineoplaston A5, Adv. Exptl. Clin. Chemother., 6/88: 9-25, 1988.
19. Liau, M. C., Lee, S. S., and Burzynski, S. R., Hypomethylation of nucleic acids: a key to the induction of terminal differentiation, Intl. J. Exptl. Clin. Chemother., 2: 187-199, 1989.
20. Liau, M. C., and Burzynski, S. R., Separation of active anticancer components of antineoplaston A2, A3 and A5, Intl. J. Tiss. React., 12(supplement): 1-18, 1990.
21. Liau, M. C., Lee, S. S., and Burzynski, S. R., Modulation of cancer methylation complex isozymes as a decisive factor in the induction of terminal differentiation mediated by antineoplaston A5. Intl. J. Tiss. React., 12(supplement): 1-18, 1990.
22. Liau, M. C., Ashraf, A., Lee, S. S., Hendry, L. B. and Burzynski, S. R., Riboflavin as a minor active anticancer component of Antineoplaston A2 and A5, Intl. J. Tiss. React., 12(supplement): 18-26, 1990.
23. Liau, M. C., Liau, C. P., Burzynski, S. R., Potantilation of induced terminal differentiation by phenylacetic acid and related chemicals, Intl. J. Exptl. Clin. Chemother., 8: 9-17, 1992.
24. Liau, M. C., Luong Y., Liau C. P., and Burzynski, S. R., Prevention of drug-induced DNA hypermethylation by antineoplaston components, Intl. J. Exptl. Clin. Chemother., 5: 19-23, 1992b.
25. Muindi, J. R. F., Frankel, S. R., Huselton, C., Degrazia, F., Garland, W. A., Young, C. W., and Warrell, R. P., Clinical pharmacology of oral all-trans retinoic acid in patients with acute promyelocytic leukemia, Cancer Res., 52: 2138-2142, 1992.
26. Muldoon, T. G, Copland, J. A., Hendry, L. B., Antineoplaston A10 activity on carcinogen-induced rat mammary tumors, Intl. J. Tiss. React., 12(supplement): 51-56, 1990.
27. Toniola, D., Weiss, H. K., and Basilio, C. A., Temperature sensitive mutation affecting 28S ribosomal RNA production in mammalian cells, Proc. Natl. Acad. Sci. USA, 70: 1273-1277, 1973.
28. Warrell, R. P. Jr., Frankel, S. R., Miller, W. H., Jr. Sheinberg, D. A., Itri, L. M., Hettelman, W. N., Vyas, R., Andreeff, M., Tafuri, A., Jakubowski, A, Gabrilove, J., Gordon, M. S., and Dmitrovsky, E., Differentiation therapy of acute promyelocytic leukemia with tretinoin (all-trans-retinoic acid), N. Engl. J. Med., 324: 1385-1393, 1991.
29. Spielholz, C., Golde D. W., Houghton, A. N., Nualart, F., and Vera, J. C., Incicased facilitated transport of dehydroascorbic acid without changes in sodium-dependent ascorbate transport in human melanoma cells, Cancer Res., 57: 2529-2537, 1997.
30. Mr. Rentaro Sano, Annihilating Cancer, Shimao Publisher, Taipei, Taiwan, 1997, pp 202-203.

SUMMARY OF THE INVENTION

The invention provides a pharmaceutical composition that can induce cancer cell to differentiate, and the use thereof in treating and preventing cancer. As mentioned above, cancer includes a variety of very complicated diseases. However, a common feature of cancers is that all cancer cells are capable of perpetual cell division, and cannot undergo terminal differentiation. Surprisingly, the inventor of the present invention found that abnormal ternary methylation enzymes were the major cause of cancer, therefore a new strategy to treat and prevent cancer was developed based on this finding.

After extensive study over more than 30 years, the inventor of the present invention found that ternary methylation enzymes were the major cause of cancer. It is the abnormality of these enzymes that renders cancer cells immortal. The ternary methylation enzymes play a very important role in cell division and differentiation. Cells are induced to divide when the activity of these enzymes is increased. On the contrary, cells are induced to synthesize methyl-deficient nucleic acids when the activity of these enzymes decrease, thereby are induced to differentiate into terminally differentiated cells, which are no longer capable of dividing. All cancer cells have abnormal ternary methylation enzymes, and the activity of these enzymes is high in these cells, thus making these cells divide endlessly. Clearly, abnormal ternary methylation enzymes are the cause of cancer. Therefore, an inhibitor of these abnormal enzymes can effectively fight against cancer and can effectively prevent healthy cells to become cancer cells. As a matter of fact, there are enough natural chemical substances in the body of a healthy person to inhibit the formation of abnormal ternary methylation enzymes. Therefore, carcinogenesis takes a very long period of time. In this period, the patient gradually accelerates the excretion of the anticancer chemicals. When the anticancer chemicals decrease to a concentration insufficient to inhibit the abnormal ternary methylation enzymes, the cancer cells take root to develop. Healthy persons excrete a small amount of anticancer substances in the urine. Upon purification, the anticancer substances can selectively inhibit the abnormal ternary methylation enzymes, thus inducing cancer cells to differentiate as normal cells. These naturally occurring anticancer substances do not affect the growth and the function of normal cells, thus the patients will not suffer from adverse effect. This strategy of therapy is thus called "differentiation therapy".

Generally, the excretion of the anticancer substances can be balanced by the production of such substances in the body of a healthy person, thus sufficient amount of such substances is maintained in the body to keep a check on the evolution of cancer cells. In contrast, a patient suffering from cancer excretes much more of the anticancer substances, and gradually loses the ability to control the evolution of cancer cells. The inventor of the present invention has isolated and purified the anticancer substances, i.e. the cell differentiation agent, from the urine of healthy persons. The cell differentiation agent can transform the abnormal ternary methylation enzymes to their normal forms, induce cancer cells to undergo terminal differentiation, and/or apoptosis. In this way cancer can be treated or prevented.

The active components in cell differentiation agent include differentiation inducers and differentiation helper inducers. The differentiation inducer can antagonize the abnormal protein factor bonded to ternary methylation enzymes, which is present specifically in cancer cells. Differentiation helper inducer is the inhibitor of the component enzymes of the ternary methylation enzymes, which can potentiate the action of the differentiation inducer. Accordingly, the differentiation helper inducer is essential in the "differentiation therapy", although to a lesser extend compared with the differentiation inducer. In the cell differentiation agent according to the present invention, the differentiation inducers are PP-0 and OA-0.79, and the differentiation helper inducers include 4-hydroxyphenylacetic acid, hippuric acid, 5-hyrdroxyindole acetic acid, uroerythrin and riboflavin. PP-0 is a peptide conjugated with a pigment material which emerges from a gel filtration column of Ultrogel AcA202 with a $K_{av}$ value of 0. OA-79 is an organic acid which emerges from the same gel column with a $K_{av}$ value of 0.79.

In addition, the cell differentiation agent according to the present invention also comprises another component, i.e. anticachexia agent, which is also helpful to the cancer treatment. It is found that phenylacetyl glutamine has the ability to reverse excessive excretion caused by the cachexia of cancer patient [Mr. Liau M. C., (Same invention of this patent application case), et al., 1987; Muldoon et al., 1990, ref. 10 and 26], which is the main component of fraction 4 in FIG. 2. This component is helpful to the treatment of cancer because most cancer patients have developed the symptom of cachexia. Briefly, the cell differentiation agent can provide an excellent therapeutic effect when a variety of active components are combined to produce synergistic effect.

It is found that the cell differentiation agent can provide a better anticancer effect when used in combination with other cytotoxic drugs such as thymidine.

It is found that the cell differentiation agent can provide a much better anticancer effect when used in combination with vitamin C and vitamin $B_{17}$.

The cell differentiation agent according to the present invention is prepared by collecting normal human urine for the purification of anticancer components that includes ultrafiltration, reverse phase chromatography, evaporation and freeze drying. The product of the present invention can be prepared as a injection formulation, or capsule.

Compared with prior art, the advantage of the present invention is utilizing anticancer substances that naturally exist in human bodies, and the treatment is directed to the root of the disease by making cancer cells differentiate and stop dividing. Therefore, the present invention is an effective therapy aimed at the elimination of the cause of the disease, and the medicine according to the present invention has no adverse effect.

These features and advantages of the present invention will be fully understood and appreciated from the following detailed description of the accompanying Drawings.

BRIEF DESCRIPTION OF THE DRAWINGS

The above object and the content of the present invention will become more apparent by describing in detail preferred examples thereof with reference to the attached drawings in which.

Figure 6:
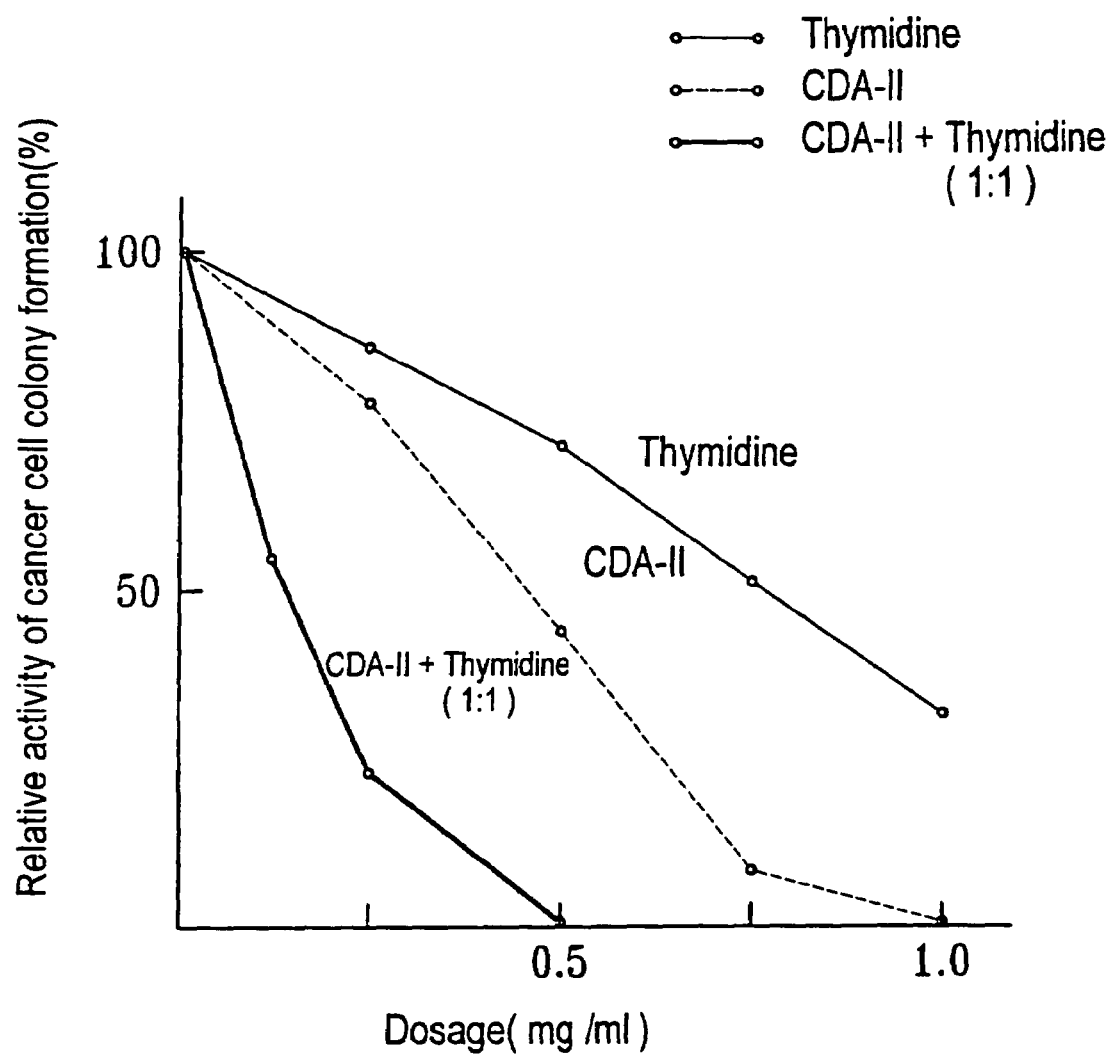
FIG. 6 shows the synergistic anticancer action between CDA-II of the present invention and thymidine, the abscissa represents dosage (mg/ml), the ordinate represents the relative activity (%) of the cancer cell colony formation. O—O represents the group in which thymidine is used alone; O . . . O represents the group in which CDA-II is used alone; O—.—.—O represents the group in which thymidine and CDA-II are used together (1:1).

The activity of cancer cell colony formation is determined by using HBL-100 breast cancer cells according to the method described in Example 4, which is expressed by the percentage of the activity of cancer cell colony formation in a control group in which none of the chemicals is added. A group in which thymidine is used alone, a group in which CDA-II is used alone, and a group in which thymidine and CDA-II are used together (1:1) were tested. The result is shown in FIG. 6, which demonstrates that the combined administration give a better therapeutic effect than single administration of CDA-II or thymidine. The synergistic effect is remarkable.

Figure 7:
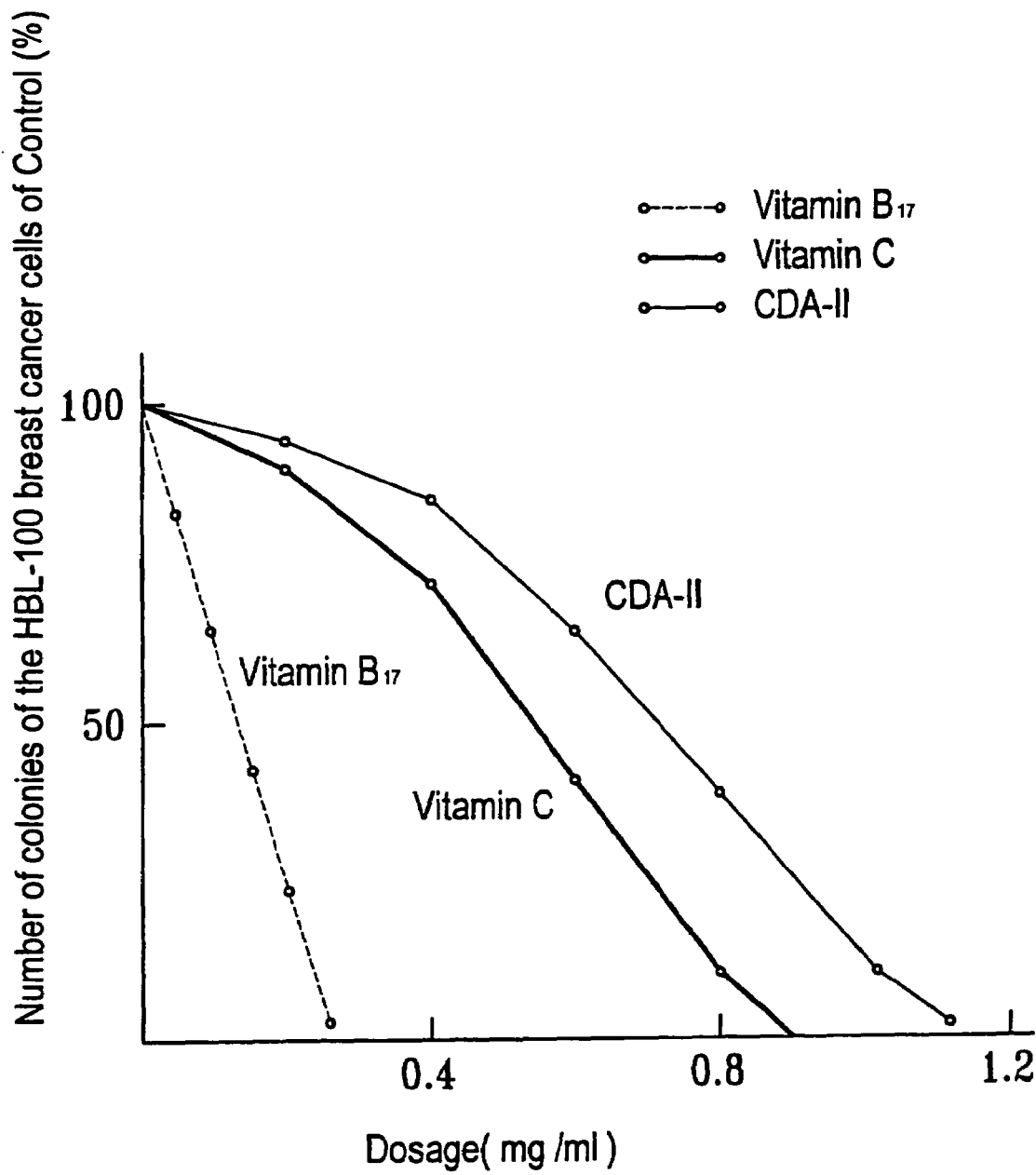

FIG. 7 shows the anticancer effect of CDA-II, antioxidant vitamin C, and vitamin $B_{17}$. The activity of cancer cell colony formation is determined by using HBL-100 breast cancer cells according to the method described in Example 4. Each culture flask contains 5 ml medium, which contains 3000 HBL-100 cells and different amounts of CDA-11, vitamin C or vitamin $B_{17}$. After incubation at 37° C. for 5 days, the cells were stained with Giemsa, and numbers of colonies with more than 8 cells were counted under a microscope.

In the present invention, AdoHcy represents S-adenosyl-homocysteine, and SAHH represents S-adenosylhomocysteine hydrolase.

DETAILED DESCRIPTION OF THE PREFERRED EMBODIMENT

Figure 1:
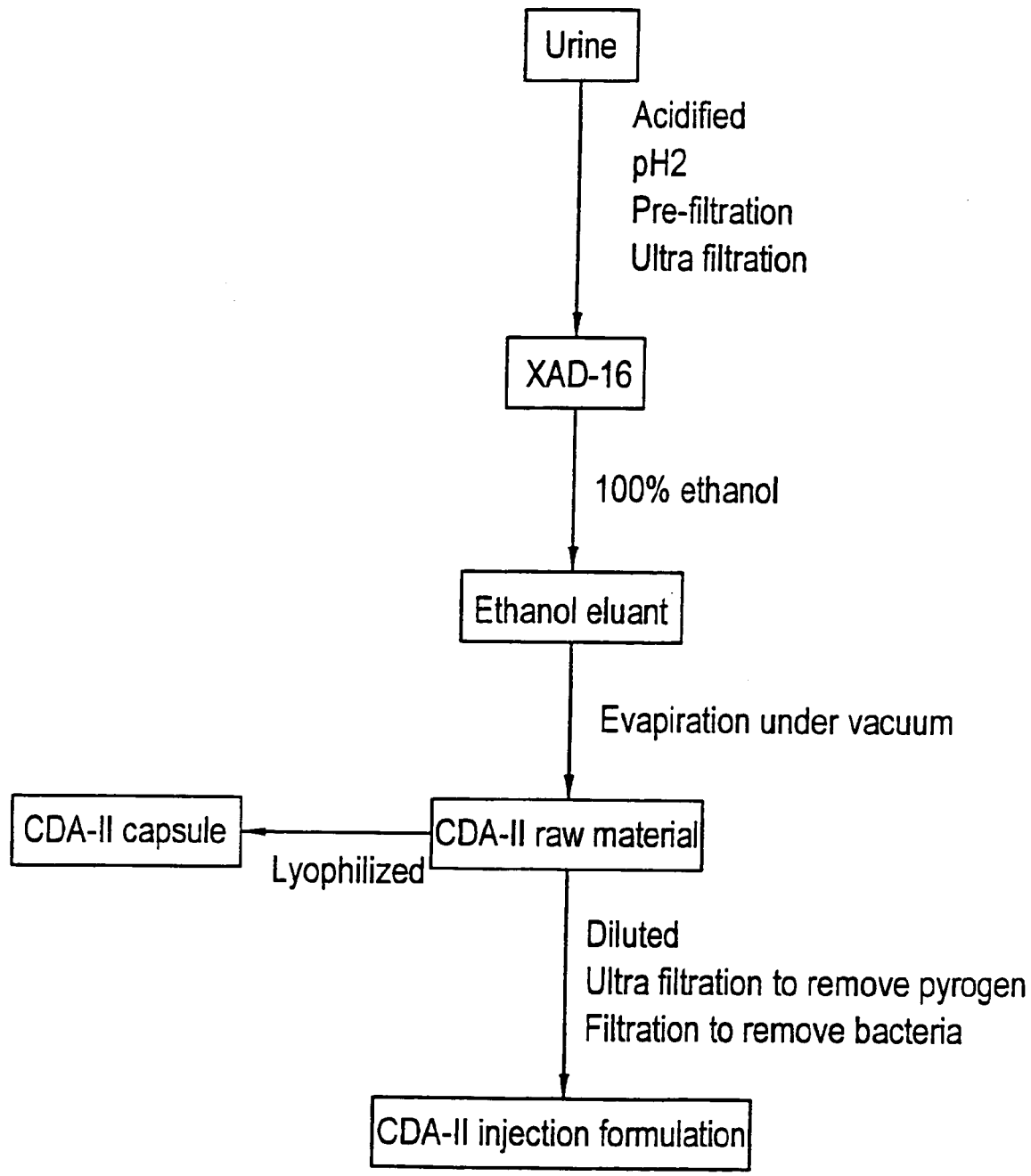
FIG. 1 is a flow chart showing the process for the preparation of cell differentiation agent according to the present invention.

The process for the preparation of cell differentiation agent according to the present invention is illustrated in FIG. 1. While the present invention is described further referring to the examples below, it is not intended to limit the scope of the invention.

EXAMPLE 1

Preparation of Cell Differentiation Agent

The process for the preparation of cell differentiation agent includes collection of urine, filtration, adsorption, solvent extraction and drying. An aqueous solution without pyrogen was used as the raw material of CDA-II.

When conducting the collection of urine, 1N HCl was added into the collection container in a proportion of 1 liter of HCl to 20 liters of urine. The purpose for this is to maintain the activity of the differentiation agent, which in this way can be maintained at least one month. The urine was filtrated through a nylon cloth after the pH was adjusted to 2, then the substances with molecular weight over 10,000 Dalton were removed by ultra filtration (Millipore filter or the like can be used). Adsorbent XAD-16 (Sigma) was placed in a hop-pocket, and then the hop-pocket was placed in a plastic funnel. Before the adsorbent was put into use, it was washed with 2 volume/weight (v/w) ethanol, then with 2 (v/w) deionized water to remove ethanol, and this step was repeated twice. After the urine had passed through the absorbent XAD-16, it was washed with 4 (v/w) deionized water, and then was eluted with 2 (v/w) ethanol. The ethanol eluant was neutralized, and ethanol was removed by evaporation under vacuum, while the temperature was kept below 50° C. The dried substance was dissolved in distilled water and was used as the raw material of CDA-II.

After elution with ethanol, the adsorbent was washed with 2 (v/w) deionized water, the absorbent can be used in a new cycle of absorption, until the adsorption capacity decreases to about 70% of that of a new adsorbent. Generally, XAD-16 can be reused about 200 times.

Because human body excretes daily a definite amount of creatinine, and the concentration of solid substances in urine is proportional to the amount of creatinine, thus, the quantitation of the chemicals in urine is based on the amount of creatinine. In the urine collected and used in this example, the concentration of creatinine is in the range of 1.2-3.7 g/l, the average of it is 2.4±0.6 g/l. In the first 100 cycles of adsorption, the yield of CDA-II is about 0.51±0.17 g/g creatinine, and the solid substance in urine is about 46.7 g/g creatinine. Therefore, the yield of the CDA raw material is about 1.1% of the solid substances.

EXAMPLE 2

The Preparation of the Injection Formulation of Cell Differentiation Agent

The final concentration of CDA-II in the injection formulation is 40±2 mg/ml, while the concentration of CDA-II in the raw material is above 250 mg/ml. Therefore, the raw material is required to be diluted to the final concentration of the injection formulation. After dilution with distilled water from which pyrogen was removed, the raw material was subjected to a series of filtration. First, the raw material was filtrated with a filter paper, then was filtrated through Millipore membrane filters with pore sizes of 1 μm and 0.45 μm, respectively, and finally was filtrated with a Millpore Pellicone system to remove pyrogen. After adjusted to the desired concentration with deionized water without pyrogen, the solution was passed through a filter with a pore size of 0.22 μm within 8 hours in a sterilized operating room (class 100 decontaminated chamber) to accomplish sterilization filtration. Then, the filtrate was prepared as a 100 ml or a 250 ml differentiation agent injection formulation.

EXAMPLE 3

The Preparation of Cell Differentiation Agent Capsule

After the raw material was filtrated sequentially through a paper filter, and Millipore membranes filters with pore size of 1 μm and 0.45 μm, respectively, the filtrate was dried by lyophilization. The dried material was ground, then packaged with an automatic capsule machine into capsules of 500 mg in weight. Then the capsules were packaged with aluminum foil, and sterilized by radiation.

EXAMPLE 4

Assay of the Anticancer Activity of Cell Differentiation Agent

The anticancer effect of cell differentiation agent is assessed based on the inhibition of the abnormal ternary methylation enzymes of cancer cells, the induction of cancer cells to undergo terminal differentiation, and the termination of cancer cells to divide. That is to say, cell differentiation agent can inhibit the abnormal enzyme $MAT^{LT}$ (methionine adenosyltransferase) of cancer cells, induce the differentiation of HL-60 cancer cells, and inhibit the formation of human breast cancer cell colony. These methods have been described [Liau, et al., 1977a, 1988, 1990a, ref. 13, 18, 20] Three aliquots of CDA-II were used to analyze its anticancer activity, as is described below:

CDA-II injection formulation was used in a dosage of 1 mg/ml. $MAT^{LT}$ was obtained from HL-60 cancer cell. First, the precipitated cells were suspended in a solution of 0.05M Tris, pH 7, 0.5 mM $MgCl_2$, and then the cells were homogenized with Dounce homogenizer. The enzyme solution was separated by high-speed centrifugation (226,000×g, 0.5 hr). The enzyme was purified by DEAE-cellulose chromatography, and $MAT^{LT}$ was eluted with a KCl gradient solution and purified [Liau, et al., 1977a, ref. 13]. The activity of $MAT^{LT}$ was determined as previously described [Liau, et al., 1977a, ref. 13]. The 0.05 ml reaction solution containing 0.05 M Tris, pH 8.2, 15 M KCl, 15 mM $MgCl_2$, 5 mM DTT (dithiothreitol), 2 mM ATP and 1 μM [$^3$H—$CH_3$] methionine was incubated at 37° C. for 30 minutes to allow reaction to proceed. The reaction was stopped with 0.4M PCA. The supernatant was then transferred to cellulose phosphate paper of 1 square inch. The paper was put into a beaker and washed with 5 mM phosphate buffer, pH 7 to remove unreacted [$^3$H—$CH_3$] methionine. Finally, the radiation of adsorbed [$^3$H—$CH_3$] AdoMet (S-adenosyl methionine) was measured to determine the activity of $MAT^{LT}$ (the result is shown in table 1).

The terminal differentiation of HL-60 cancer cells was analyzed by NBT+ method [Liau, et al., 1988a, ref. 18]. At the beginning, the HL-60 cells were diluted to $1.5\times10^5$ cells/ml each-culture flask. After incubation for 96 hours, an aliquot was taken from each culture flask for the determination of cell concentration. Another aliquot was centrifuged to pellet the cells, then the cell pellet was suspended in NBT solution and incubated at 37° C. for 30 min. An aliquot was placed in a hemocytometer for the determination of differentiation. The total number of cells and the cells stained as black (NBT+) were counted under a microscope. The percentage of NBT+ indicates the activity of CDA-II to induce cell differentiation.

Another indication of the anticancer activity of CDA-II is the inhibition of colony formation of HBL-100 breast cancer cell. At the beginning, the breast cancer cells growing at the exponential phase were washed with HBS solution, then about 2 ml 0.05% trypsin-0.53 mM EDTA was added, and the solution was incubated at 37° C. for 10 minutes. Thereafter, the cell density was measured, then an aliquot was taken and diluted to $3\times10^3$ cells/ml. 0.5 ml of the diluted solution was added into 4.5 ml culture medium with or without CDA-II and incubated at 37° C. Five days later, the medium was discarded, and the cells were washed with isotonic saline, then methanol was added to fix cells for 15 minutes. The fixed cells were stained for 30 minutes with Giemsa staining solution diluted 20 fold. After the staining solution was discarded, the cells were washed with water and dried. The colony number above 8 cells was counted under a microscope to determine the anticancer activity of CDA-II (the result is shown in table 1).

EXAMPLE 5

Characterization of the Active Components in Cell Differentiation Agent

Figure 2:
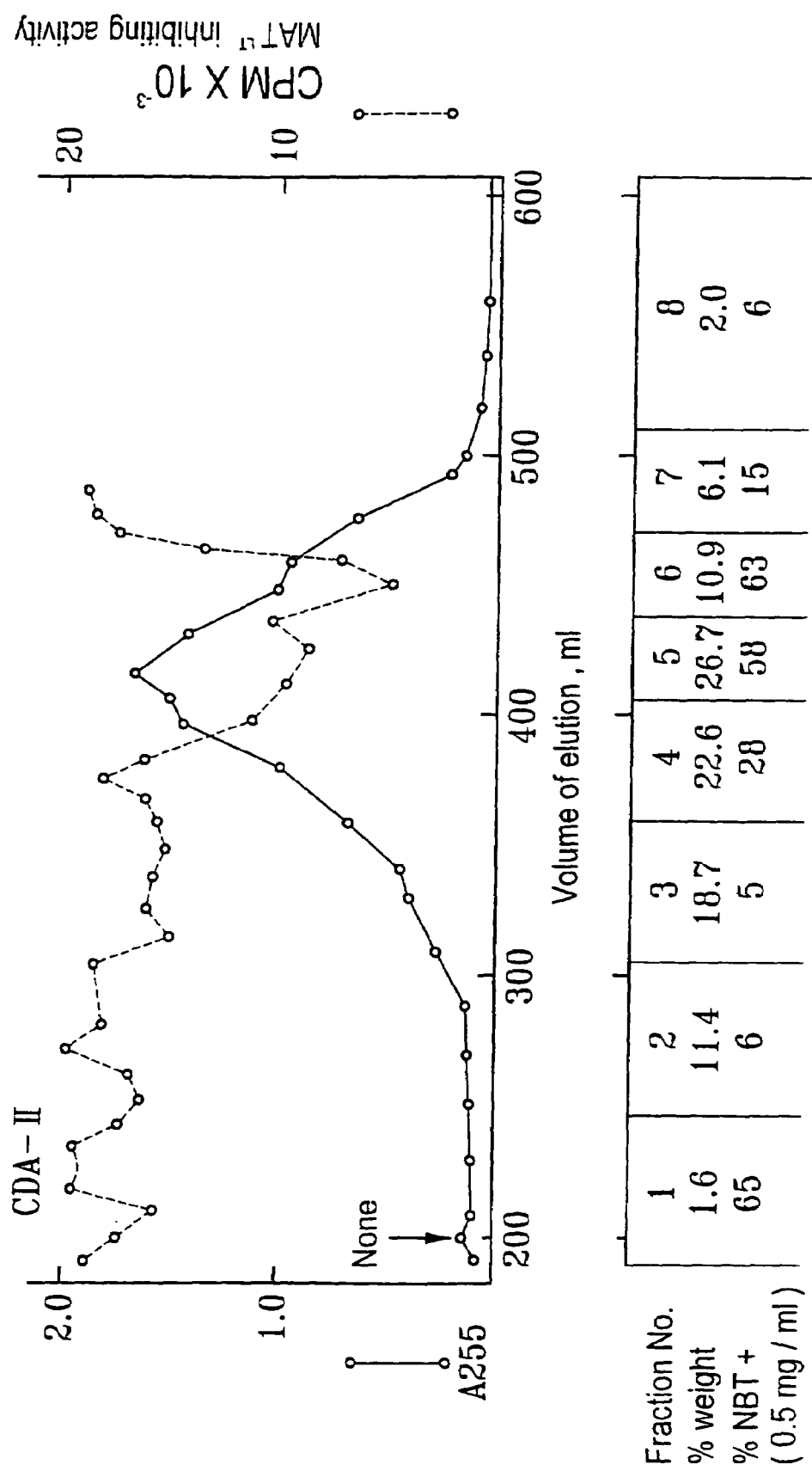
FIG. 2 shows the cell differentiation agent of the present invention analyzed by the gel filtration. After concentration by lyophilization, the CDA-II injection formulation was separated through column chromatography, in which Bio-Gel P2 chromatographic column (4.1 cm×44 cm) was used. The fractions collected were measured the OD value at $A_{255nm}$ (O—O), the inhibition of $MAT^{LT}$ activity (O . . . O), weight percent, and differentiation activity on HL-60 cancer cells (represented by % $NBT^+$).

The CDA-II cell differentiation agent injection formulation prepared in Example 2 was lyophilized and concentrated to 200 mg/ml. 5 ml of the concentrated solution was added onto a Bio-Gel P2 chromatographic column (4.1 cm×44 cm), then the column was eluted with distilled water. The fractions were collected every 7 minutes into a test tube, which is 10 ml in volume. After the completion of the elution, 25 μl of the eluant from each of the test tube was taken, and diluted with water to 1 ml to determine OD at $A_{255nm}$. Another 25 μl of the eluant was taken from each tube to determine the inhibition of $MAT^{LT}$ activity. The $MAT^{LT}$ activity was measured according to the method described in Example 4. The eluant was separated into 8 fractions as shown in FIG. 2 based on the OD at $A_{255nm}$. Each fraction was lyophilized and weighed to determine the weight distribution. The dry solid was dissolved in distilled water to determine the differentiation inducing activity of HL-60 cancer cells, which is represented by % NBT+. The differentiation inducing activity is measured according to the method described in example 4, and the result is shown in FIG. 2.

Of the active anticancer components in cell differentiation agent, the most important one is the differentiation inducer that induces cell to differentiate. The separation, purification and its action have been described [Liau, et al., 1988; 1989; 1990a; 1990b; ref. 18, 19, 20, 21]. The differentiation inducers comprise two major components; one of them is an acidic peptide conjugated with pigment, abbreviated as PP-0, the other one is an organic acid, abbreviated as OA-0.79. PP-0 is in the first fraction shown in FIG. 2, OA-0.79 is in the fifth and sixth fractions. The active fractions obtained form the Bio-Gel P2 chromatographic column were separately fractionated by gel filtration on a column of Ultrogel AcA202 (60-140 μm, 2.5 cm×58 cm, was obtained from LKB) as described in a separated paper (18). PP-0 is a peptide conjugated with a pigment material which emerges from a gel filtration column of Ultrogel AcA202 with a $K_{av}$ value of 0. OA-79 is an organic acid which emerges from the same gel column with a $K_{av}$ value of 0.79. It should be noted that the demonstrated differentiation activity of the cell differentiation agent does not reflect the activity of the cell differentiation inducer itself, but is contributed by the synergy with the differentiation helper inducers. Surprisingly, differentiation helper inducers are the main components in the cell differentiation agent, the content of the differentiation inducers is very low. Because they have not been sufficiently purified to be characterized, the chemical structure of which is still unknown. As is shown in FIG. 2, the cell differentiation inducing activity coincides with the activity of $MAT^{LT}$ inhibition. However, in some fractions, such as fraction 2 and fraction 3 have noticeable $MAT^{LT}$ inhibition activity, but have no activity to induce cancer cells to differentiate. Probably these fractions comprise only differentiation helper inducers, and no differentiation inducer, therefore have no activity to induce cancer cells to differentiate.

The differentiation helper inducers are the inhibitors of the component enzymes of the ternary methylation enzymes [Liau, et al., 1992a, ref. 23], which assists the differentiation inducer in transforming the abnormal ternary methylation enzymes to their normal forms, therefore potentiates the differentiation action of the differentiation inducer.

It is known that MAT inhibitors in CDA include phenylacetic acid, indole acetic acid and hippuric acid. Phenylacetic acid, which is found in fraction 6 and fraction 7 in FIG. 2, is probably the product resulted from the hydrolysis during the drying process of phenylacetyl glutamine, which can be identified with C18 HPLC (High Performance Liquid Chromatography). Indole acetic acid is also found in these fractions. Hippuric acid is the major component in fraction 5. To reach 0.5 reductive index (i.e., the effective dose of the differentiation inducer is reduced to 50% of it), the concentration of these MAT inhibitors are 4 mM phenylacetic acid, 8 mM hippuric acid, and 0.95 mM indole acetic acid. As the differentiation helper inducer, the inhibitor of methyltransferase is much more effective than the inhibitor of MAT. To achieve a certain effect, the amount required for the inhibitor of methyltransferase is only one thousand or less of the amount of the inhibitor of MAT. It is known that there are two inhibitors of methyltransferase in CDA, both of them have excellent activities as the differentiation helper inducers. The two inhibitors are vitamin $B_2$ and uroerythrin. Vitamin $B_2$ is found in the latter half of fraction 8 in FIG. 2, as is described above [Liau, et al., 1990C, ref. 22]. This component, which is yellow in color, can be purified into vitamin $B_2$ by C18 HPLC, and the content of which is about 0.04% of the CDA-II. Uroerythrin is found in fraction 6 and fraction 7 in FIG. 2. High purity of uroerythrin can be obtained by Sephadex SH chromatography and silica gel thin layer chromatography, and the content of which is about 0.5% of the CDA-II. Because it is hard to avoid loss during purification, and CDA-II preparation has a remarkable red color, the content of uroerythrin may be more than 0.5%.

EXAMPLE 6

The Determination of the Activity of Uroerythrin and Vitamin $B_2$ as Differentiation Helper Inducers The action of the differentiation helper inducer was determined according to the method designed by the present inventor of this application case, Dr. Ming C. Liau [Liau, et al., 1992a, ref. 23]. The differentiation of cancer cells was measured by using leukemic cancer cells HL-60 to quantitate the NBT+ cells. First, HL-60 cells were subcultured at an initial cell density $1.5 \times 10^5$ cells/ml, 10 ml/flask. A set of four flasks were used as the control, wherein only retinoic acid was added as differentiation inducer, the amount of which was adjusted to induce NBT+ cells to the range of 15% to 60%. Another flask was used as the blank which was added the solution only. The total amount of methanol in which retinoic acid was dissolved should not exceed 2%, so as not to affect the differentiation of cancer cells. Each of other sets also comprises four flasks, which were added smaller amounts of retinoic acid, and a blank flask with only the solvent. Different amounts of the differentiation helper inducers were added in each set. The cell numbers in every flask were counted after incubation for 96 hours, and NBT was assayed according to the method of Example 4. Generally, the natural differentiation of the HL-60 cells, i.e. without the action of any of the additives, is usually lower than 4%. In the sets containing only differentiation helper inducer, the differentiation of cells is less than 10%. The value of NBT+ in each flask is required to subtract the value of the blank control.

The value of $ED_{50}$, i.e., the amount of the differentiation inducer required when NBT+ is 50%, can be obtained by plotting the amount against NBT+. The reductive index can be calculated from the $ED_{50}$ value. Reductive index=$ED_{50}$ in the presence of differentiation helper inducer/$ED_{50}$ with cell differentiation inducer only. The lower the reductive index, the higher the activity of the differentiation helper induced.

Figure 3:
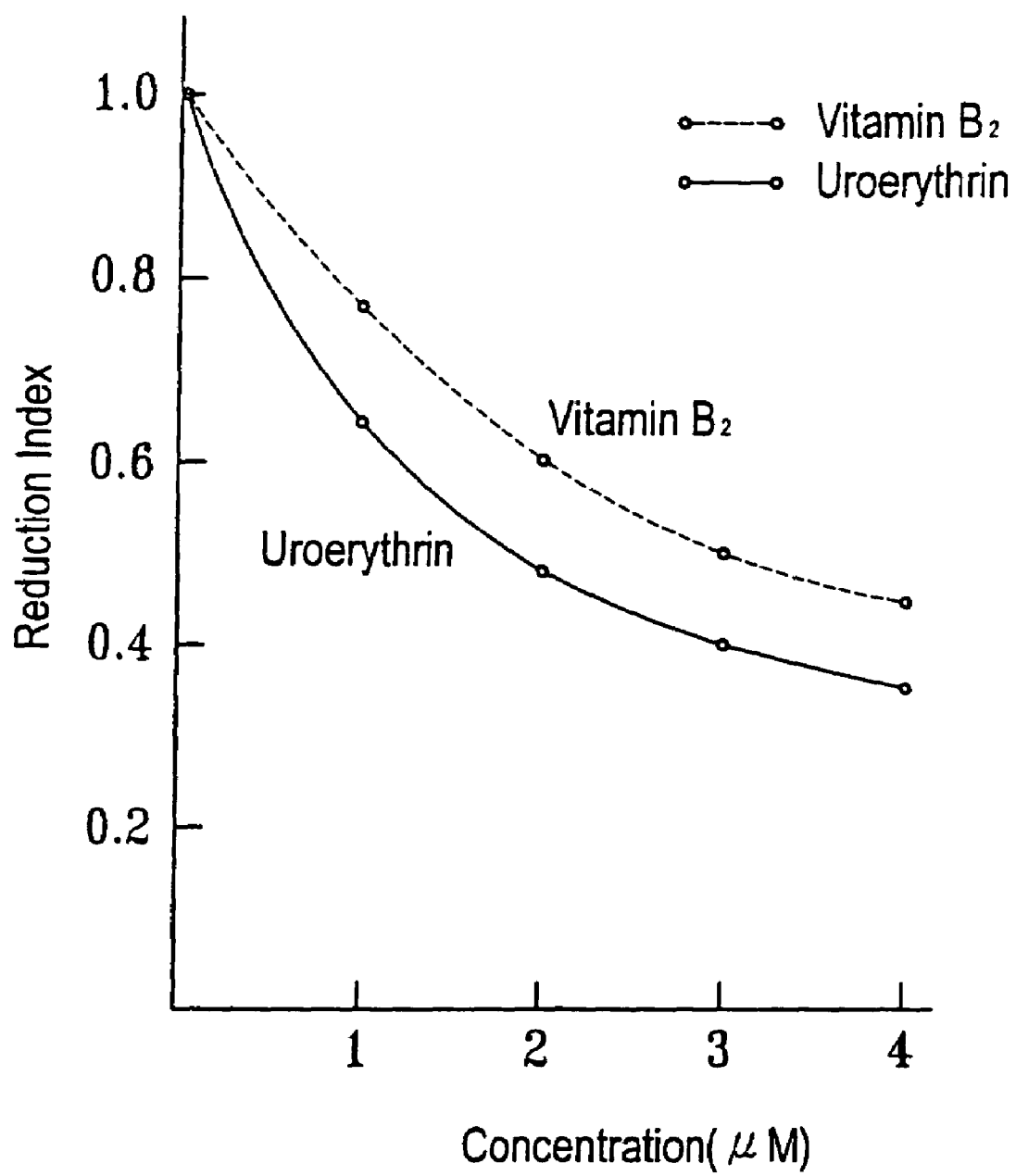
FIG. 3 shows the relationship between the concentration of uroerythrin (O—O) and vitamin $B_2$ (O . . . O) as differentiation helper inducers and the decrease index.

As can be seen from FIG. 3, the concentrations of vitamin $B_2$ and uroerythrin are 3.0 μM and 1.8 μM, respectively, to reach the 0.5 reductive index, which are much lower than the MAT inhibitors mentioned above.

EXAMPLE 7

Figure 4:
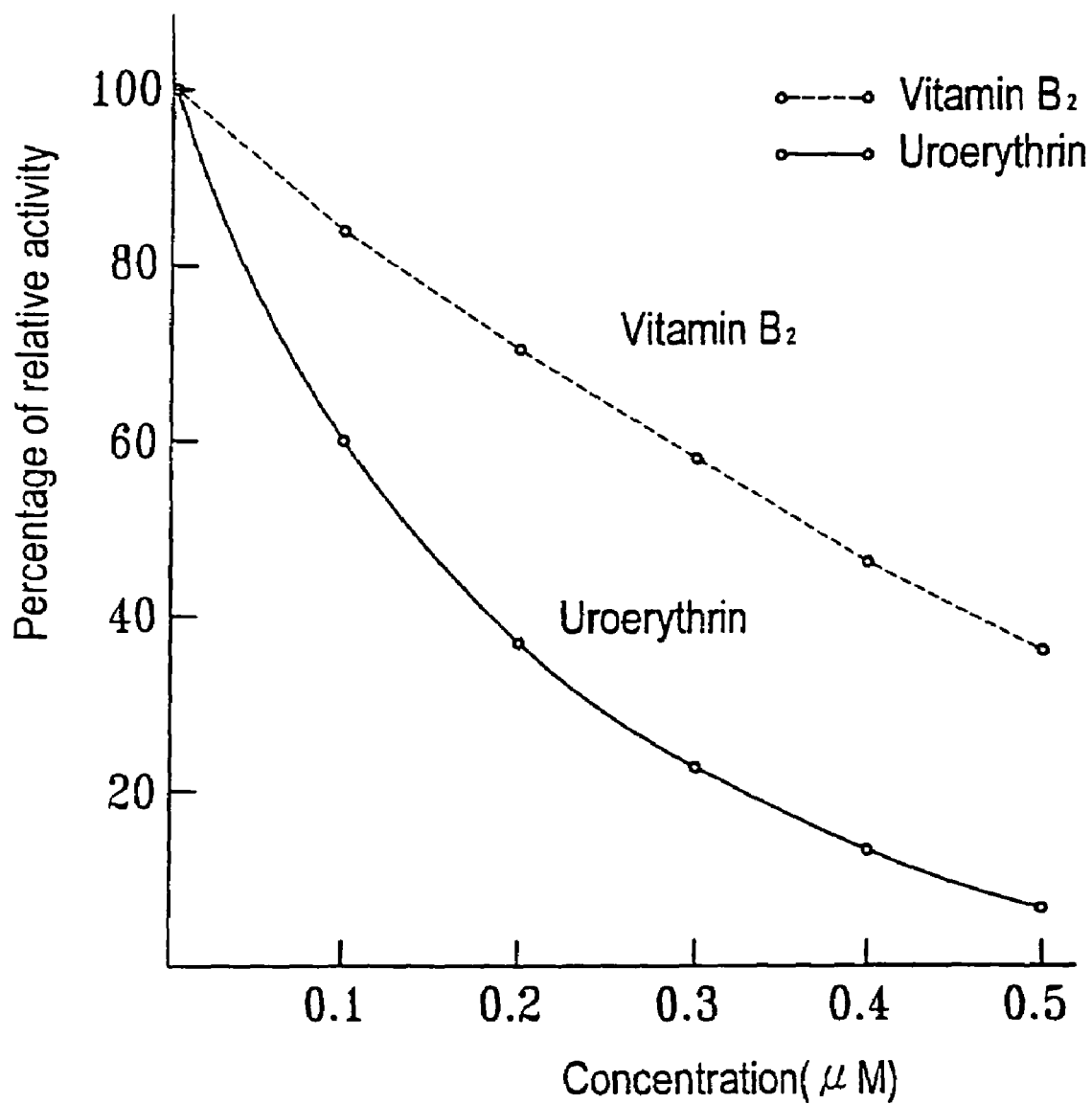
FIG. 4 shows the relationship between the concentration of uroerythrin (O—O) and vitamin $B_2$ (O . . . O) and the inhibition activity toward tRNA methyltransferases.

The Inhibition Activity of Uroerythrin and Vitamin $B_2$ on tRNA Methyltransferase tRNA methyltransferases were prepared from the high speed supernatant of HL-60 cancer cells shown in Example 4. First, the supernatant was adjusted to pH 5, and the proteins precipitated were separated by centrifugation, then dissolved in 0.05M Tris, pH 7.8, 0.5 mM $MgCl_2$ and 5 mM $HSCH_2CH_2OH$. After the solution passed though DEAE-cellulose column, tRNA methyltransferase were purified by KCl gradient [Liau, et al., 1977b, ref. 14]. The activity of tRNA methyltransferases were determined in 0.25 ml reaction solution comprising 0.05M Tris, pH 7.8, 0.1M $NH_4Cl$, 0.04M $NH_4F$, 0.5 mM $MgCl_2$, 5 mM DTT, 20 μg *Escherichia coli* B tRNA, 0.25 μCi [$^3H$—$CH_3$] AdoMet (S-adenosylmethionine) and 25 μg enzymes. The reaction is carried at 37° C. for 30 minutes. tRNA was precipitated with cold 5% TCA (trichloroacetic acid), then was collected on Millipore membrane (pore size is 0.45 μm). After the membrane was dried, the radiation was assayed to determine the activity of tRNA methyltransferases, and the result is shown in FIG. 4.

The effective amount to inhibit tRNA methyltransferases is much lower than the effective amount as the differentiation helper inducer. The reason for this is possibly related to the physical and chemical conditions for measuring these different activities. Different physical and chemical conditions (such as the concentration of salts) may affect differently the effective contact between chemicals and enzymes. Despite the differences in sensitivity, the activities of different tRNA methyltransferase inhibitors are proportional to the activities of differentiation helper inducers. The tRNA methyltranferase inhibitor with higher activity is a better differentiation helper inducer. We have also found that other tRNA methyltransferase inhibitors, such as ethidium bromide and hycanthone [Liau, et al., 1977b, ref. 14], are excellent differentiation helper inducers as uroerythrin and vitamin $B_2$. The concentration of ethidium bromide and hycanthone is 0.95 μM and 2 μM, respectively, to reach 0.5 reductive index. Therefore, it is no doubt that the inhibitors of methyltransferases can be used as effective differentiation helper inducers.

EXAMPLE 8

Analysis of the Differentiation Helper Inducers to Promote Differentiation

Differentiation helper inducers can not only decrease the effective amount of the differentiation inducer, but also promote the completeness of differentiation. HL-60 cancer cells were subcultured at an initial cell density of $1.5 \times 10^5$ cells/ml. The culture flasks were grouped into three sets; each set includes 4-5 flasks. One flask was used as the blank without additives. One set was added 0.025-0.15 μM retinoic acid as the control; the other two sets were added 4 μM of uroerythrin or vitamin $B_2$. NBT test was conducted as described in Example 4 after incubation for 96 hours. The values thus obtained were subtracted with the value obtained by the blank without additives.

Figure 5:
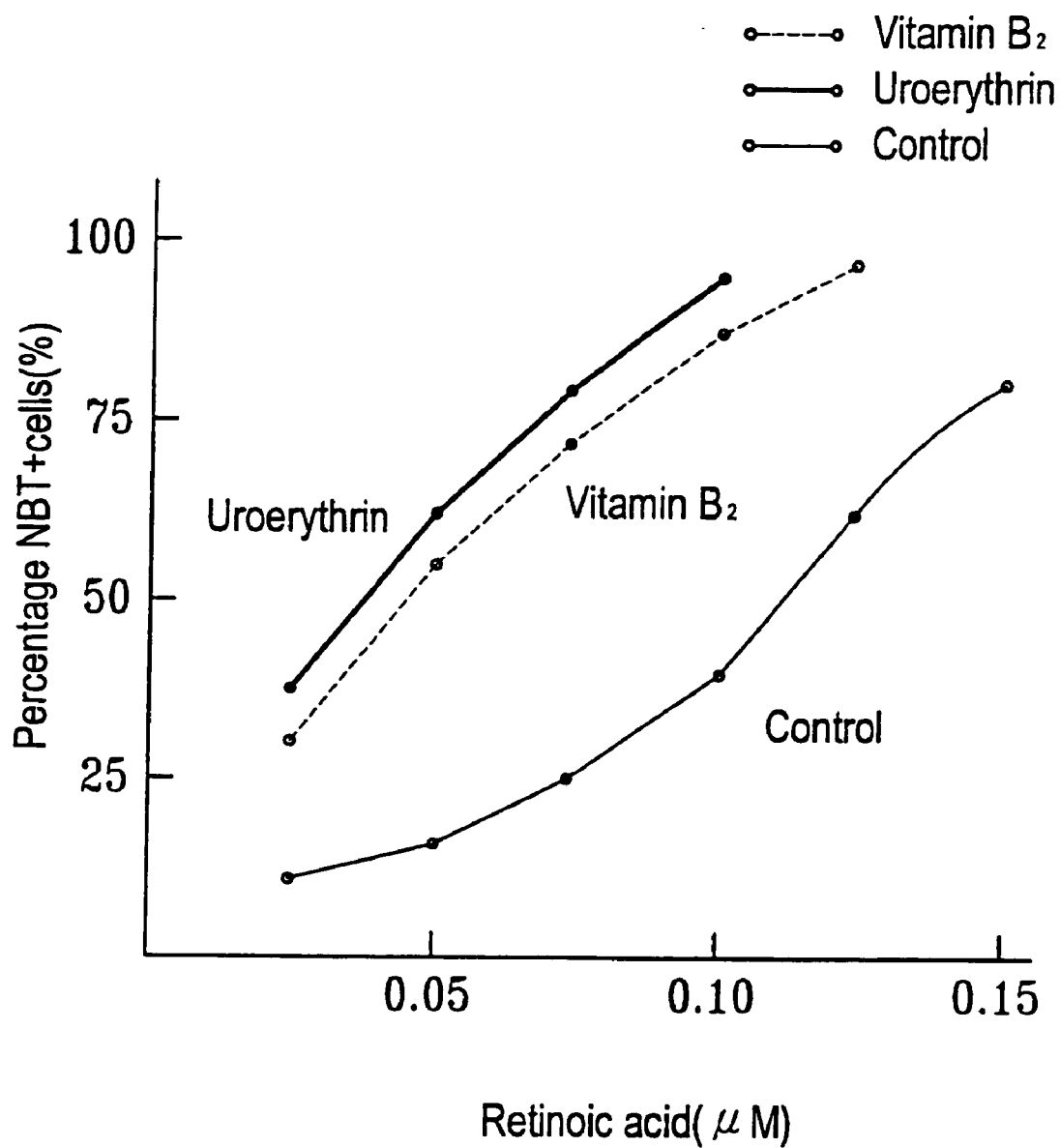
FIG. 5 shows the enhancement of uroerythrin and vitamin $B_2$ to the activity of differentiation inducer, the abscissa represents the concentration of retinoic acid μM), the ordinate represents the percentage of NBT (nitroblue tetrazolium)+ cells. O—O represents the control group in which different concentrations of retinoic acid are added; O . . . O represents the group in which 4 μM vitamin $B_2$ are added. O—.—.—O represents the group in which 4 μM uroerythrin are added.

As can be seen from FIG. 5, the extent of differentiation only reached about 85% when the differentiation inducer is used alone. When combined with uroerythrin or vitamin $B_2$, the extent of differentiation reached 100%. It is much more important to achieve the completeness of differentiation than to decrease the effective amount of the differentiation inducer.

EXAMPLE 9

Synergistic Anticancer Action of Cell Differentiation Agent with Other Chemical Anticancer Agent Ternary methylation enzyme is very active in cancer cells. If DNA synthesis is inhibited by chemicals, over-transfer of methyl is resulted, and genes are repeatedly synthesized. Repeated synthesis of genes result in the formation of drug resistant cells (Liau, et al., 1992b, ref. 24), and this is one of the important reasons causing the failure of chemotherapy.

The formation of drug resistant cells can be minimized through inhibition of the abnormal ternary methylation enzymes by using cell differential agent, which is helpful to the treatment of cancer. It has been demonstrated that cell differentiation agent can enhance the therapeutic effect of some anticancer drugs, for example, as is shown with the combination of CDA-II and thymidine in the present invention (FIG. 6).

EXAMPLE 10

The Combination of the Anticancer Action of Cell Differentiation Agent and Antioxidants Hypoxia can stimulate apoptosis and result in the death of cancer cells. The utilization of vitamin C and vitamin $B_{17}$ to create a hypoxia state is especially suitable for the treatment of cancer. Cancer cells are capable of absorbing vitamin C 10-fold more than normal cells [ref. 29], while vitamin $B_{17}$ can be selectively decomposed by β-glucosidase present only in cancer cells to yield toxic cyanide, which inhibits the activity of oxidase [ref. 30]. β-glucosidase is highly active in cancer cells, but is much less active normal cells. As is shown in FIG. 7, CDA-II, vitamin C and vitamin $B_{17}$ can inhibit the formation of colonies of HBL-100 human breast cancer cells, and the $IC_{50}$ of which is 0.69, 0.53 and 0.13 mg/ml, respectively. The result of combined use of CDA-II and vitamin C or vitamin $B_{17}$ is shown in table 2, which demonstrates that the combined use of CDA-II and vitamin C or vitamin $B_{17}$ is additive.

TABLE 1

The anticancer action of cell differentiation agent (CDA-II)

| Lot No. | % MAT inhibiton | % NBT+ | % Inhibition to the colony formation of breast cancer cells |
|---|---|---|---|
| 01 | 49 | 58 | 100 |
| 02 | 55 | 53 | 100 |
| 03 | 50 | 54 | 100 |

Notes:
CDA-II used is inhection formulation, the dosage of which is 1 mg/ml.
$MAT^{LT}$ was prepared from HL-60 cancer cells by purification through DEAE-cellulose chromatography and the activity was determined as previously described [Liau, et al., 1977a, ref. 13].
The terminal differentiation of HL-60 cancer cells was determined according to the NBT+ method [18].
The inhibition of colony formation of cancer cells was determined by cell culture using human HBL-100 breast cancer cells [Liau, et al., 1990a, ref. 20].

TABLE 2

The additive action of CDA-II and vitamin C or vitamin $B_{17}$

The colony formation of HBL-100 cells: inhibition percentage Combined administration

| Drugs & dosages | mg/ml | Administered alone | Predicted value | Measured value |
|---|---|---|---|---|
| CDA-II | 0.4 | 16 | 28 | 39 |
| C | 0.2 | 12 | | |
| CDA-II | 0.6 | 38 | 50 | 58 |
| C | 0.2 | 12 | | |
| CDA-II | 0.8 | 65 | 77 | 80 |
| C | 0.2 | 12 | | |
| CDA-II | 0.4 | 16 | 36 | 39 |
| $B_{17}$ | 0.05 | 20 | | |
| CDA-II | 0.6 | 38 | 58 | 58 |
| $B_{17}$ | 0.05 | 20 | | |
| CDA-II | 0.8 | 65 | 85 | 83 |
| $B_{17}$ | 0.05 | 20 | | |

The experiment was carried out according to FIG. 6. HBL-100 cells were cultured with different dosages of CDA-II, vitamin C and vitamin $B_{17}$ alone, and with the combination of CDA-II and vitamin C, or the combination of CDA-II and vitamin $B_{17}$.

The present invention may be embodied in other specific forms without departing from the spirit of the essential attributes thereof, therefore, the illustrated embodiment should be considered in all respects as illustrative and not restrictive, reference being made to the appended claims rather than to the foregoing description to indicate the scope of the invention.

INDUSTRIAL APPLICABILITY

Compared with prior art, the advantage of the present invention is utilizing the anticancer substances naturally occurring in human bodies to treat and prevent cancer, thereby making the cancer cells to differentiate and stop dividing. Therefore, the present invention is an effective treatment to eliminate the cause of the disease present only in cancer cells, and the medicine according to the present invention has no adverse effect.

Many changes and modifications in the above described embodiment of the invention can, of course, be carried out without departing from the scope thereof. Accordingly, to promote the progress in science and the useful arts, the invention is disclosed and is intended to be limited only by the scope of the appended claims.

What is claimed is:

1. A method for the preparation of an anti-cancer cell differentiation agent pharmaceutical composition, comprising the steps of:
   (1) collecting human urine, in which the concentration of creatinine is in the range of 1.2-3.7 g/l, and acidifying the urine;
   (2) filtering the collected urine to remove substances with a molecular weight greater than about 10,000 Daltons;
   (3) passing the collected and filtered urine through an adsorbent to yield an adsorbed urine derivative;
   (4) extracting the adsorbed urine derivative with an organic solvent; and
   (5) diluting the extracted adsorbed urine derivative with water, and removing pyrogens by ultrafiltration through a filter, to yield thereby the anti-cancer cell differentiation agent pharmaceutical composition comprising a predetermined amount of differentiation inducers, wherein the differentiation inducers are PP-0 and OA-0.79, wherein PP-0 is a peptide conjugated with a pigment material which emerges from a gel filtration column of Ultrogel AcA202 with a $K_{av}$ value of 0, and OA-79 is an organic acid which emerges from the same gel column with a $K_{av}$ value of 0.79.

2. The method for the preparation of an anti-cancer cell differentiation agent pharmaceutical composition according to claim 1, wherein the adsorbed urine derivative is extracted with an organic solvent after washing the adsorbed urine derivative with deionized water and eluting the adsorbed urine derivative with ethanol that is then removed by evaporation.

3. The method for the preparation of an anti-cancer cell differentiation agent pharmaceutical composition according to claim 1, wherein the extracted adsorved urine derivative is diluted with deionized water to a concentration in an approximate range of 40 to 50 mg/ml.

4. The method for the preparation of an anti-cancer cell differentiation agent pharmaceutical composition according to claim 1, wherein the pyrogens are removed by ultrafiltration through a filter with a pore size of approximately 0.22 μm.

5. The method for the preparation of an anti-cancer cell differentiation agent pharmaceutical composition according to claim 1, wherein the anti-cancer cell differentiation agent pharmaceutical composition further comprises:

a predetermined amount of differentiation helper inducers, wherein the differentiation helper inducers include 4-hydroxyphenylacetic acid, hippuric acid, 5-hyrdroxyindole acetic acid, uroerythrin and riboflavin.

6. The anti-cancer cell differentiation agent pharmaceutical composition prepared according to claim 5, wherein the composition is formulated for one of parenteral or oral administration.

7. The anti-cancer cell differentiation agent pharmaceutical composition according to claim 5, further comprising at least one of a vitamin C and a vitamin $B_{17}$.

* * * * *

UNITED STATES PATENT AND TRADEMARK OFFICE
CERTIFICATE OF CORRECTION

PATENT NO. : 7,232,578 B2  Page 1 of 1
APPLICATION NO. : 11/106620
DATED : June 19, 2007
INVENTOR(S) : Ming-Cheng Liau It is certified that error appears in the above-identified patent and that said Letters Patent is hereby corrected as shown below:

Title Page,

Item (62) please insert the following:

--Related U.S. Application Data Continuation-in-Part of Application No. 10/293,292, filed on November 14, 2002, now abandoned.--

Signed and Sealed this

Eighteenth Day of December, 2007

JON W. DUDAS
*Director of the United States Patent and Trademark Office*